US012569575B2

(12) United States Patent (10) Patent No.: US 12,569,575 B2
Mehta et al. (45) Date of Patent: Mar. 10, 2026

(54) RADIOPAQUE PARTICLE COMPOSITIONS AND USES THEREOF

(71) Applicant: GUSTAVE ROUSSY TRANSFERT, Villejuif (FR)

(72) Inventors: AMi Mehta, Coto de Caza, CA (US); Anup Dasnurkar, Rancho Santa Margarita, CA (US)

(73) Assignee: GUSTAVE ROUSSY TRANSFERT, Villejuif (FR)

( * ) Notice: Subject to any disclaimer, the term of this patent is extended or adjusted under 35 U.S.C. 154(b) by 830 days.

(21) Appl. No.: 17/672,046

(22) Filed: Feb. 15, 2022

(65) Prior Publication Data

US 2022/0273825 A1 Sep. 1, 2022

Related U.S. Application Data

(60) Provisional application No. 63/149,834, filed on Feb. 16, 2021.

(51) Int. Cl.
| | |
|---|---|
| *A61K 49/04* | (2006.01) |
| *A61K 9/00* | (2006.01) |
| *A61K 31/282* | (2006.01) |
| *A61K 31/404* | (2006.01) |
| *A61K 31/44* | (2006.01) |
| *A61K 31/4439* | (2006.01) |
| *A61K 31/47* | (2006.01) |
| *A61K 31/496* | (2006.01) |
| *A61K 31/506* | (2006.01) |
| *A61K 31/517* | (2006.01) |
| *A61K 31/5377* | (2006.01) |
| *A61K 31/7068* | (2006.01) |
| *A61K 47/44* | (2017.01) |

(52) U.S. Cl.
CPC ........ *A61K 49/0423* (2013.01); *A61K 9/0019* (2013.01); *A61K 31/282* (2013.01); *A61K 31/404* (2013.01); *A61K 31/44* (2013.01); *A61K 31/4439* (2013.01); *A61K 31/47* (2013.01); *A61K 31/496* (2013.01); *A61K 31/506* (2013.01); *A61K 31/517* (2013.01); *A61K 31/5377* (2013.01); *A61K 31/7068* (2013.01); *A61K 47/44* (2013.01); *A61K 49/0404* (2013.01); *A61K 49/0442* (2013.01)

(58) Field of Classification Search
CPC .............. A61K 49/0423; A61K 9/0019; A61K 31/282; A61K 31/404; A61K 31/44; A61K 31/4439; A61K 31/47; A61K 31/496; A61K 31/506
See application file for complete search history.

(56) References Cited

U.S. PATENT DOCUMENTS

| | | | | |
|---|---|---|---|---|
| 5,827,531 A | * | 10/1998 | Morrison ............. | A61K 9/5073 424/490 |
| 2008/0009902 A1 | * | 1/2008 | Hunter ................. | A61K 9/0024 606/228 |
| 2010/0021550 A1 | * | 1/2010 | Li .......................... | A61L 24/001 424/493 |
| 2013/0251786 A1 | * | 9/2013 | Li .......................... | A61K 38/47 424/94.5 |
| 2017/0321054 A1 | * | 11/2017 | Guo ....................... | C08G 69/40 |
| 2021/0113463 A1 | * | 4/2021 | Deschamps ............ | A61K 9/107 |

* cited by examiner

*Primary Examiner* — Jianfeng Song
(74) *Attorney, Agent, or Firm* — B. Aaron Schulman, Esq.; Stites & Harbison, PLLC

(57) ABSTRACT

Compositions and emulsions are described, which are useful in treating disease.

16 Claims, No Drawings
Specification includes a Sequence Listing.

SEQUENCE LISTING

```
<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Biodegradable linkage GPQGIASQ

<400> SEQUENCE: 1

Gly Pro Gln Gly Ile Ala Ser Gln
1               5

<210> SEQ ID NO 2
<211> LENGTH: 7
<212> TYPE: PRT
<213> ORGANISM: Artificial Sequence
<220> FEATURE:
<223> OTHER INFORMATION: Biodegradable linkage GPQGAGQ

<400> SEQUENCE: 2

Gly Pro Gln Gly Ala Gly Gln
1               5

<210> SEQ ID NO 3
<211> LENGTH: 7
<212> TYPE: PRT
<213> ORGANISM: Artificial Sequence
<220> FEATURE:
<223> OTHER INFORMATION: Biodegradable linkage GPQPAGQ

<400> SEQUENCE: 3
```

```
Gly Pro Gln Pro Ala Gly Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Biodegradable linkage KPLGLKARK

<400> SEQUENCE: 4

Lys Pro Leu Gly Leu Lys Ala Arg Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Biodegradable linkage GPQIWGQ

<400> SEQUENCE: 5

Gly Pro Gln Ile Trp Gly Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Biodegradable linkage QPQGLAK

<400> SEQUENCE: 6

Gln Pro Gln Gly Leu Ala Lys
1               5

<210> SEQ ID NO 7
<211> LENGTH: 10
<212> TYPE: PRT
<213> ORGANISM: Artificial Sequence
<220> FEATURE:
<223> OTHER INFORMATION: Biodegradable linkage GFQGVQFAGF

<400> SEQUENCE: 7

Gly Phe Gln Gly Val Gln Phe Ala Gly Phe
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Biodegradable linkage GFGSVQFAGF

<400> SEQUENCE: 8

Gly Phe Gly Ser Val Gln Phe Ala Gly Phe
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Biodegradable linkage GFGSYFFAGF

<400> SEQUENCE: 9
```

-continued

```
Gly Phe Gly Ser Thr Phe Phe Ala Gly Phe
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Biodegradable linkage GGLGPAGGK

<400> SEQUENCE: 10

Gly Gly Leu Gly Pro Ala Gly Gly Lys
1               5

<210> SEQ ID NO 11
<211> LENGTH: 4
<212> TYPE: PRT
<213> ORGANISM: Artificial Sequence
<220> FEATURE:
<223> OTHER INFORMATION: Biodegradable linkage APGL

<400> SEQUENCE: 11

Ala Pro Gly Leu
1

<210> SEQ ID NO 12
<211> LENGTH: 4
<212> TYPE: PRT
<213> ORGANISM: Artificial Sequence
<220> FEATURE:
<223> OTHER INFORMATION: Biodegradable linkage GFLG

<400> SEQUENCE: 12

Gly Phe Leu Gly
1

<210> SEQ ID NO 13
<211> LENGTH: 5
<212> TYPE: PRT
<213> ORGANISM: Artificial Sequence
<220> FEATURE:
<223> OTHER INFORMATION: Biodegradable linkage DEVDT

<400> SEQUENCE: 13

Asp Glu Val Asp Thr
1               5

<210> SEQ ID NO 14
<211> LENGTH: 10
<212> TYPE: PRT
<213> ORGANISM: Artificial Sequence
<220> FEATURE:
<223> OTHER INFORMATION: Biodegradable linkage GFGSYFFAGF

<400> SEQUENCE: 14

Gly Phe Gly Ser Tyr Phe Phe Ala Gly Phe
1               5                   10
```

RADIOPAQUE PARTICLE COMPOSITIONS AND USES THEREOF

RELATED APPLICATIONS

This application claims priority of U.S. Provisional Patent Application No. 63/149,834, the entire content of which is herein incorporated by reference.

SEQUENCE LISTING

This application contains a sequence listing having the filename MV_217_ST25.txt, which is 2,892 bytes in size, and was created on Feb. 16, 2021. The entire content of this sequence listing is herein incorporated by reference.

FIELD

The disclosure herein relates generally to vascular treatment compositions and emulsions or nanoparticles, and their methods of to treat vascular disorders or conditions.

BACKGROUND

Embolization is widely used to treat vascular malformations, such as aneurysms, arteriovenous malformations, fistulas, and tumors. These malformations can be treated with a variety of different products, including metallic coils, polymer-metal hybrid coils, microparticles, glues, and foams. For example, transarterial chemoembolization is recommended for patients with intermediate stage disease (e.g., intermediate stage liver disease). Conventional transarterial chemoembolization involves the injection of chemotherapeutic agents mixed with lipiodol. This leads to necrosis of the target tumors by cytotoxic and ischemic effects. However, lipiodol is not an embolic agent. In order to create an ischemic effect, physicians may embolize the vessels afterwards with bland microspheres or gelatin foam. Embolization with particles such as microspheres or gelatin foam may lead to non-target embolization or inadvertent downstream embolization, depending on the particle size distribution. In addition, lipiodol does not release drugs in a controlled and sustained manner. The elution of a drug is similar to a bolus release and can contribute to large systemic exposure of chemotherapeutics, causing undesirable side effects. Thus, there remains a need for products that can minimize the risks associated with embolization and release drugs in a controlled and sustained manner.

SUMMARY

Compositions and emulsions are described that comprise: a water-soluble pharmaceutical ingredient; an oil based media; a biodegradable or bioresorbable radiopaque polymeric particle including a visualization agent and a polymer. In some embodiments, the polymer includes a biodegradable linkage to the visualization agent. In some embodiments, the composition does not include a visualization agent. In some embodiments, the oil based media is a poppy seed oil, a component thereof, or a combination of components thereof. In some embodiments, the particle is a nanoparticle (e.g., about 100 nm to about 500 nm). In some embodiments, the visualization agent is a polymerized visualization agent including a radiopaque material covalently linked to its matrix, or a particle that encapsulates a radiopaque material that is not covalently linked to its matrix.

The visualization agent can be a particulate and can have a concentration of about 5% w/w to about 65% w/w. Depending on the type of imaging used with the present compositions, the visualization agent can be an iodinated compound, a metal particle, barium sulfate, superparamagnetic iron oxide, a gadolinium molecule or a combination thereof.

In one embodiment, the compositions or emulsions provided herein are useful for treating a vascular disease. Thus, methods of treating a vascular disorder or condition in a subject in need thereof are described herein, comprising administering a composition or emulsion described herein to the subject, thereby treating the vascular disorder or condition. In some embodiments, methods of treating a vascular disorder in a subject in need thereof are described herein, comprising: providing a composition or an emulsion described herein; inserting a delivery device into a vessel of the subject; guiding the delivery device to an area in the subject in need of treatment; injecting the liquid embolic polymer composition through the delivery device into the vessel at the area in need of treatment thereby forming a polymeric mass through which blood may flow; and treating the vascular condition.

DETAILED DESCRIPTION

Described herein generally are vascular treatment compositions and emulsions or nanoparticles comprising: a pharmaceutical ingredient; poppy seed oil, a component thereof, or a combination of components thereof; a biodegradable radiopaque polymeric particle including a polymer, or, for example, a chitosan or glutaraldehyde based particle; and optionally a visualization agent that can permit visualization in vivo. In some embodiments, these compositions and emulsions or nanoparticles can be introduced through a delivery device in a fluid state and transition to a loosely agglomerated state once in the body. In some embodiments, the pharmaceutical ingredient is a water-soluble pharmaceutical ingredient. In some embodiments, the embolic effect of the materials provided herein has a duration of about 24 hours or less. In some embodiments, the embolic effect of the materials provided herein lasts for more than 24 hours.

Thus, in some embodiments, provided herein are compositions comprising:

a pharmaceutical ingredient;

poppy seed oil, a component thereof (e.g., palmitic acid, stearic acid, oleic acid, linoleic acid, myristic acid, heptadecanoic acid, arachidic acid, γ-tocopherol, or glyceride (e.g., saturated dilinolein, oleo-dilinolein, or trilinolein)), or a combination of components thereof;

a biodegradable radiopaque polymeric particle including a visualization agent (which is optional), and including: PLGA (poly(lactic-co-glycolic acid)) monomer; PLLA (poly-L-lactide) monomer; PLLA monomer and PLA (polylactide) monomer; PEG (polyethylene glycol) diacrylamide monomer, glycerol monomethacrylate monomer, 2-amino ethyl methacrylate monomer, and N,N-methylenebisacrylamide monomer; PEG diacrylamide monomer, amino propyl methacrylamide monomer, and 3-sulfopropyl acrylate potassium salt monomer; or PCL (polycaprolactone) monomer and gelatin.

In some embodiments, the PEG diacrylamide monomer is a PEG 10,000 diacrylamide monomer.

In some embodiments, the water-soluble pharmaceutical ingredient is axitinib, bosutinib, cabozantinib, canertinib, dasatinib, dovitinib, doxorubicin, epirubicin, erlotinib, gefitinib, gemcitabine, idarubicin, imatinib, lapatinib, lestaurtinib, lenvatinib, masitinib, nilotinib, pazopanib, rego-rafenib, sorafenib, sunitinib, terazosin, vandetanib, vatalanib, oxaliplatin, carboplatin, or a pharmaceutically acceptable salt thereof.

In some embodiments, the pharmaceutical ingredient is axitinib, bosutinib, cabozantinib malate, canertinib diHCl, dasatinib, dovitinib, doxorubicin HCl, epirubicin HCl, erlo-tinib HCl, gefitinib, gemcitabine, idarubicin HCl, imatinib methane-sulfonate, lapatinib toluene-sulfonate, lestaurtinib, lenvatinib mesylate, masitinib, nilotinib, pazopanib, rego-rafenib, sorafenib, sunitinib, terazosin, vandetanib, or vatalanib diHCl. In some embodiments, the water-soluble phar-maceutical ingredient is oxaliplatin, carboplatin, or a pharmaceutically acceptable salt thereof. In some embodi-ments, the pharmaceutical ingredient is doxorubicin or a pharmaceutically acceptable salt thereof (e.g., doxorubicin HCl).

In some embodiments, the pharmaceutically acceptable salt is a methane-sulfonate (e.g., a mono-methane-sulfonate salt) or an HCl salt (e.g., a mono-HCl or di-HCl salt). In some embodiments, the pharmaceutical ingredient is one or more of the drugs provided in Table 1.

TABLE 1

| Solubility of drugs. | | | |
|---|---|---|---|
| Drug | Indication/Uses | Solubility in DMSO | Solubility in Water |
| Doxorubicin HCl | Transarterial chemoembolization (TACE) for hepatocellular carcinoma (HCC) Acute lymphoblastic leukemia (ALL) Acute myeloid leukemia (AML) Breast cancer (lymph nodes) (metastatic) Gastric (stomach) cancer that is metastatic Hodgkin lymphoma Neuroblastoma that is metastatic Non-Hodgkin lymphoma Non-small cell lung cancer that is metastatic Ovarian cancer that is metastatic Small cell lung cancer that is metastatic Soft tissue and bone sarcomas that are metastatic Thyroid cancer that is metastatic Transitional cell bladder cancer that is metastatic Wilms tumor that is metastatic | 100 mg/mL | 10 mg/mL |
| Epirubicin HCl | TACE for HCC Breast cancer (lymph nodes) | 10 mg/mL | 10 mg/mL |
| Idarubicin HCl | TACE for HCC Acute myeloid leukemia (AML) | 10 mg/mL | 1 mg/mL |
| Cabozantinib malate | HCC Medullary thyroid cancer that is progressive and has metastasized Renal cell carcinoma that is advanced | 18 mg/mL | |
| Levatinib mesylate | HCC Renal cell carcinoma Thyroid cancer | 9 mg/mL | |
| Regorafenib | Colorectal cancer that has metastasized Gastrointestinal stromal tumor that is local advanced, cannot be removed by surgery, or has metastasized HCC | 97 mg/mL | |
| Axitinib | Renal cell carcinoma that is advanced | 77 mg/mL | |
| Bosutinib | Chronic myelogenous leukemia (CML) that is Philadelphia chromosome positive | 100 mg/mL | |
| Canertinib diHCl | Esophageal squamous cell carcinoma | >5.6 mg/mL | 10 mg/mL |
| Dasatinib | Acute lymphoblastic leukemia that is Philadelphia chromosome positive Chronic myelogenous leukemia (CML) that is Philadelphia chromosome positive | 98 mg/mL | |
| Dovitinib | Bladder Cancer | 40 mg/mL | |
| Erlotinib HCl | Non-small cell lung cancer (NSCLC) that is metastatic and has certain EGFR gene mutations Pancreatic cancer | 20 mg/mL | |
| Gefitinib | Non-small cell lung cancer (NSCLC) that has metastasized | 20 mg/mL | |
| Imatinib methane-sulfonate | Acute lymphoblastic leukemia in adults and children that is Philadelphia chromosome positive Chronic eosinophilic leukemia or hypereosinophilic syndrome | 100 mg/mL | 200 mg/mL |

TABLE 1-continued

| | | Solubility in DMSO | Solubility in Water |
|---|---|---|---|
| Drug | Indication/Uses | | |
| | Chronic myelogenous leukemia that is Philadelphia chromosome positive Dermatofibrosarcoma protuberans Gastrointestinal stromal tumor (GIST) Myelodysplastic/myeloproliferative neoplasms Systemic mastocytosis | | |
| Lapatinib toluene-sulfonate | Breast cancer that is advanced or has metastasized | 200 mg/mL | |
| Lestaurtinib | Acute leukemias and some other types of cancer | 44 mg/mL | |
| Masitinib | Melanoma Multiple myeloma Gastrointestinal cancer Pancreatic cancer Alzheimer disease Multiple sclerosis Rheumatoid arthritis Mastocytosis Amyotrophic lateral sclerosis | >95 mg/mL | <1.2 mg/mL |
| Nilotinib | Chronic myelogenous leukemia (CML) that is Philadelphia chromosome positive | 50 mg/mL | |
| Pazopanib | Renal cell carcinoma that is advanced Soft tissue sarcoma that is advanced | 95 mg/mL | |
| Sorafenib | Hepatocellular carcinoma that cannot be removed by surgery Renal cell carcinoma that is advanced Thyroid cancer in certain patients with progressive, recurrent, or metastatic disease | 92 mg/mL | |
| Sunitinib | Renal cell carcinoma (RCC) Pancreatic cancer Gastrointestinal stromal tumor (GIST) Imatinib-resistant GIST | 100 mg/mL | 2 mg/mL (in citrate buffer) |
| Vandetanib | Medullary thyroid cancer Medullary thyroid cancer that cannot be removed by surgery and is locally advanced or has metastasized | 30 mg/mL | 5 mg/mL (in pH 6.5) |
| Vatalanib diHCl | Metastatic colorectal cancer | 85 mg/mL | 10 mg/mL |
| Gemcitabine | Breast cancer Ovarian cancer Non-small cell lung cancer Pancreatic cancer Bladder cancer | 5 mg/mL | 25 mg/mL |
| Terazosin | Benign prostatic hyperplasia Hypertension | | 20 mg/mL |

In some embodiments, the visualization agent is an iodinated compound, barium sulfate, superparamagnetic iron oxide, a gadolinium molecule, or a combination thereof. In some embodiments, the visualization agent has a concentration of about 5% to about 65%.

In some embodiments, the biodegradable radiopaque polymeric particle includes iodine or barium sulfate, and PLGA monomer.

In some embodiments, the biodegradable radiopaque polymeric particle is a biodegradable radiopaque polymeric nano-particle.

In some embodiments, the ratio of oil to particle is about 1:2 to 2:1 (e.g., 1:2, 1:1, or 2:1). In some embodiments, modulating the ratio of oil to particle will modulate the rate at which the pharmaceutical ingredient elutes from the composition.

In some embodiments, the particles are hydrophobic.

In some embodiments, provided herein are emulsions that include the compositions provided herein. In some embodiments, the emulsion is a Pickering emulsion.

Also provided herein are methods of treating a vascular disorder in a subject in need thereof, comprising:

providing a composition or emulsion described herein;

inserting a delivery device into a vessel of the subject;

guiding the delivery device to an area in the subject in need of treatment;

injecting the liquid embolic polymer composition through the delivery device into the vessel at the area in need of treatment thereby forming a polymeric mass through which blood may flow; and treating the vascular condition.

In some embodiments, the vascular disorder is an indication described in Table 1. In some embodiments, the vascular disorder is a cancer (e.g., a cancer described in Table 1).

In some embodiments, the vessel is a vessel supplying blood to an organ where dual blood supply is not available.

In some embodiments, the polymeric mass is an agglomeration of particles, which particles may be linked by non-covalent forces.

In some embodiments, the polymeric mass is a polymeric mass through which blood flows.

Also provided herein are methods of making the compositions or emulsions as described herein.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional). In some embodiments, the compositions or emulsions further comprise a reaction product of a PLGA monomer and an initiator.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional). In some embodiments, the compositions or emulsions further comprise a reaction product of a PLLA monomer and an initiator.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional). In some embodiments, the compositions or emulsions further comprise a reaction product of a PLLA monomer and a PLA monomer and an initiator.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional), and including a reaction product of a PEG 10,000 diacrylamide monomer (28% w/w), glycerol monomethacrylate monomer (68% w/w), 2-amino ethyl methacrylate monomer (3% w/w), and N,N-methylenebisacrylamide monomer (1% w/w) initiated by ammonium persulfate and tetramethylene diamine.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional), and including a reaction product of a PEG 10,000 diacrylamide monomer (40% w/w), amino propyl methacrylamide monomer (1% w/w), and 3-sulfopropyl acrylate potassium salt monomer (59% w/w) initiated by ammonium persulfate and tetramethylene diamine.

In one embodiment, the compositions or emulsions comprise: a water-soluble pharmaceutical ingredient (i.e. oxaliplatin or doxorubicin); poppy seed oil; and a biodegradable radiopaque polymeric particle including a visualization agent (which is optional), and including a reaction product of a PCL monomer and gelatin and an initiator.

Treatment site or delivery site as used herein can be any site within a living creature. In some embodiments, the creature is a mammal such as a human. Human sites can include blood vessels, renal lumens, fatty tissue, muscle, connective tissue, cerebral spinal fluid, brain tissue, respiratory tissue, nerve tissue, subcutaneous tissue, intra atria tissue, gastrointestinal tissue, and the like, or an organ other than liver where dual blood supply is not available. In some embodiments, the site is a lung or liver.

The polymer can include a visualization agent biodegradably attached to it.

A monomer or monomers can include at least one visualization species linked to the monomer to impart visibility of the liquid embolic polymer when imaged using a medically relevant imaging technique such as fluoroscopy, computed tomography, or magnetic resonance techniques. Characteristic features of the monomers with visualization species can be cores that are visible under medically relevant imaging techniques and a polymerizable moiety attached to the core with a biodegradable linkage.

A visualization agent can also be linked after polymerization if a reactive pendent group is added to the polymerization mixture before polymerization. An exemplary reactive pendent group can be an acrylate monomer having an epoxide pendent group (e.g., glycidyl acetate) or a hydroxyl ethyl pendent group. A skilled artisan can envision other pendent groups that can be added to a formed polymer.

Visualization of the polymer under fluoroscopy and CT imaging can be imparted by the use of monomers with cores containing iodine, particularly aromatic rings with a plurality of iodine atoms. A core containing iodine can be triiodophenol. Concentrations of iodine to render the liquid embolic visible using fluoroscopy or CT imaging can range from about 10% to about 60% w/w, about 20% to about 50% w/w, or about 30% to about 40% w/w of the liquid embolic solution. Visualization of the polymer under magnetic resonance imaging can be imparted by the incorporation of monomers containing gadolinium. A visualization agent for magnetic resonance imaging can be gadolinium diethylenetriaminepentaacetic acid aminoethylmethacrylate. Concentrations of gadolinium to render the liquid embolic visible using magnetic resonance imaging can range from about 0.1% to about 1% w/w, about 0.5% to about 1% w/w, or about 0.1% to about 0.5% w/w of the liquid embolic solution.

Some monomers can include biodegradable linkages to visualization species. Biodegradable linkages can permit separation of the visualization core from the polymer. After separating from the polymer, the core can be removed by diffusion and/or by cells comprising the foreign body response to the polymer. Biodegradable linkages can be separated into two types. The two types can include those susceptible to hydrolysis and those susceptible to enzymatic action. Linkages susceptible to hydrolysis can generally include esters, polyesters, or carbonates.

The biodegradable linkages can be introduced into monomers or the polymers after formation. One skilled in the art can envision benefits to both methods of introducing biodegradable linkages into the polymers.

Ester linkages can be introduced by reacting hydroxyl groups with cyclic anhydrides, such as succinic or glutaric anhydride, or cyclic esters, such as lactide, glycolide, ε-caprolactone, and trimethylene carbonate. The rate of degradation can be controlled by ester selection and the number of esters inserted into biodegradable linkages.

Linkages susceptible to enzymatic action can include peptides that can be degraded by enzymes, such as but not limited to matrix metalloproteinases, collagenases, elastases, cathepsin, or a combination thereof. Peptide sequences degraded by matrix metalloproteinases can include Gly-Pro-Gln-Gly-Ile-Ala-Ser-Gln (SEQ ID NO:1), Gly-Pro-Gln-Pro-Ala-Gly-Gln (SEQ ID NO:2), Gly-Pro-Gln-Gly-Ala-Gly-Gln (SEQ ID NO:3), Lys-Pro-Leu-Gly-Leu-Lys-Ala-Arg-Lys (SEQ ID NO:4), Gly-Pro-Gln-Ile-Trp-Gly-Gln (SEQ ID NO:5), and Gln-Pro-Gln-Gly-Leu-Ala-Lys (SEQ ID NO:6). Peptide sequences degraded by cathepsin can include Gly-Phe-Gln-Gly-Val-Gln-Phe-Ala-Gly-Phe (SEQ ID NO:7), Gly-Phe-Gly-Ser-Val-Gln-Phe-Ala-Gly-Phe (SEQ ID NO:8), and Gly-Phe-Gly-Ser-Thr-Phe-Phe-Ala-Gly-Phe (SEQ ID NO:9). Peptide sequences degraded by collagenase can include Gly-Gly-Leu-Gly-Pro-Ala-Gly-Gly-Lys (SEQ ID NO:10) and Ala-Pro-Gly-Leu (SEQ ID NO:11). Peptide sequences degraded by papain can include Gly-Phe-Leu-Gly (SEQ ID NO:12). Peptide sequences degraded by caspase-3 can include Asp-Glu-Val-Asp-Thr (SEQ ID NO:13). Peptide sequences degraded can also include Gly-Phe-Gly-Ser-Tyr-Phe-Phe-Ala-Gly-Phe (SEQ ID NO:14). The rate of degradation can be controlled by the peptide sequence selection.

In some embodiments, polymers can be polymerized from solutions, mixtures, prepolymer solutions of monomers with ionizable moieties, solutions of monomers linked to visualization species and other monomers. The solvent used to dissolve the monomers can be any solvent that dissolves or substantially dissolves the chosen monomers. Solvents can include methanol, acetonitrile, dimethyl formamide, and dimethyl sulfoxide.

Polymerization initiators can be used to start the polymerization of the monomers in the solution. The polymerization can be initiated by reduction-oxidation, radiation, heat, or any other method known in the art. Radiation crosslinking of the monomer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the monomer solution.

Initiators can include N,N,N',N'-tetramethylethylenediamine, ammonium persulfate, benzoyl peroxides, azobisisobutyronitriles and combinations thereof. In some embodiments, the polymerization initiator can be azobisisobutyronitrile (AIBN) or a water soluble AIBN derivative (e.g., 2,2'-azobis(2-methylpropionamidine) dihydrochloride). Initiator concentrations can be from about 0.1% w/w to about 5% w/w, about 0.5% w/w to about 3% w/w, about 0.25% w/w, about 0.5% w/w, about 0.75% w/w, about 1% w/w, about 1.25% w/w, about 1.50% w/w, about 1.75% w/w, or about 2% w/w, about 3%, about 4%, or about 5% of the mass of the monomers in solution. The polymerization reaction can be performed at elevated temperatures, of about 30° C. to about 200° C., about 50° C. to about 100° C., about 50° C., about 60° C., about 70° C., about 80° C., about 90° C. or about 100° C. or can proceed at room temperature without heating. After the polymerization is completed, the polymer can be recovered by precipitation in a non-solvent and dried under vacuum.

Also provided herein are methods of administering transarterial chemoembolization in a subject in need thereof, comprising locally administering a composition provided herein to a target site (e.g., a site in the subject where a carcinoma is present) of the subject. In some embodiments, the vascular disorder in a subject being treated by the compositions provided herein includes a carcinoma. For example, hepatocellular carcinoma. In some embodiments, the subject being treated is one who has locally untreatable hepatocellular carcinoma (i.e. unresectable, not suitable for local thermal ablation, or both).

Also provided herein are methods of treating a carcinoma or cancer in a subject in need thereof, comprising locally administering a composition or emulsion provided herein to a target site (e.g., a site in the subject where a carcinoma is present) of the subject. In some embodiments, the vascular disorder in a subject being treated by the compositions provided herein includes a carcinoma. For example, hepatocellular carcinoma. In some embodiments, the subject being treated is one who has locally untreatable hepatocellular carcinoma (i.e. unresectable, not suitable for local thermal ablation, or both).

In some embodiments of the methods provided herein, the carcinoma or cancer is acute lymphoblastic leukemia (e.g., adult (e.g., a subject at least 18 years old), child (e.g., a subject less than 18 years old), or a subject that is Philadelphia chromosome positive), acute myeloid leukemia (e.g., adult (e.g., a subject at least 18 years old), child (e.g., a subject less than 18 years old), or a subject that is Philadelphia chromosome positive), bladder cancer, breast cancer (e.g., breast cancer in lymph nodes) (e.g., metastatic or advanced), bone sarcoma (e.g., metastatic), chronic eosinophilic leukemia (i.e. hypereosinophilic syndrome), chronic myelogenous leukemia (e.g., in a subject that is Philadelphia chromosome positive), colorectal cancer (e.g., metastatic), dermatofibrosarcoma protuberans, esophageal squamous cell carcinoma, gastric (stomach) cancer (e.g., metastatic), gastrointestinal cancer (e.g., gastrointestinal stromal tumor (e.g., imatinib-resistant)) (e.g. locally advanced, cannot be removed by surgery, or metastatic), hepatocellular carcinoma (e.g., cannot be removed by surgery), hodgkin lymphoma, mastocytosis, melanoma, medullary thyroid cancer (e.g., progressive and metastasized), multiple myeloma, myelodysplastic neoplasm, myeloproliferative neoplasm, neuroblastoma (e.g., metastatic), non-Hodgkin lymphoma, non-small cell lung cancer (e.g., metastatic, e.g., with EGFR gene mutation(s)), ovarian cancer (e.g., metastatic), pancreatic cancer, renal cell carcinoma (e.g., advanced), small cell lung cancer (e.g., metastatic), soft tissue sarcoma (e.g., metastatic or advanced), systemic mastocytosis, thyroid cancer (e.g. metastatic, progressive, or recurrent) (e.g., medullary), transitional cell bladder cancer (e.g. metastatic), or Wilms tumor (e.g. metastatic).

In some embodiments of the methods provided herein, the pharmaceutical ingredient is doxorubicin or a pharmaceutically acceptable salt thereof, and the carcinoma or cancer is acute lymphoblastic leukemia (e.g., adult (e.g., a subject at least 18 years old), child (e.g., a subject less than 18 years old), or a subject that is Philadelphia chromosome positive), acute myeloid leukemia, bone sarcoma (e.g., metastatic), breast cancer (e.g., breast cancer in lymph nodes) (e.g., metastatic), gastric (stomach) cancer (e.g., metastatic), hodgkin lymphoma, neuroblastoma (e.g. metastatic), non-Hodgkin lymphoma, non-small cell lung cancer (e.g., metastatic), ovarian cancer (e.g., metastatic), small cell lung cancer (e.g. metastatic), soft tissue sarcoma (e.g., metastatic), thyroid cancer (e.g., metastatic) (e.g., medullary), transitional cell bladder cancer (e.g., metastatic), or Wilms tumor (e.g., metastatic).

In some embodiments of the methods provided herein, the pharmaceutical ingredient is epirubicin or a pharmaceutically acceptable salt thereof, and the carcinoma or cancer is breast cancer (e.g., breast cancer in lymph nodes) (e.g., metastatic).

In some embodiments of the methods provided herein, the pharmaceutical ingredient is idarubicin or a pharmaceutically acceptable salt thereof, and the carcinoma or cancer is acute myeloid leukemia.

In some embodiments of the methods provided herein, the pharmaceutical ingredient is cabozantinib or a pharmaceutically acceptable salt thereof, and the carcinoma or cancer is HCC, medullary thyroid cancer (e.g., medullary thyroid cancer that is progressive and has metastasized), or renal cell carcinoma (e.g., renal cell carcinoma that is advanced).

In some embodiments of the methods provided herein, the pharmaceutical ingredient is lenvatinib or a pharmaceutically acceptable salt thereof, and the carcinoma or cancer is HCC, renal cell carcinoma, or thyroid cancer.

In some embodiments of the methods provided herein, the pharmaceutical ingredient is regorafenib or a pharmaceutically acceptable salt thereof, and the carcinoma or cancer is colorectal cancer (e.g., colorectal cancer that has metastasized), GIST (e.g., GIST that is local advanced, cannot be removed by surgery, or has metastasized), or HCC.

In some embodiments of the methods provided herein, the pharmaceutical ingredient is axitinib or a pharmaceutically acceptable salt thereof, and the carcinoma or cancer is renal cell carcinoma (e.g., renal cell carcinoma that is advanced).

In some embodiments of the methods provided herein, the pharmaceutical ingredient is bosutinib or a pharmaceutically acceptable salt thereof, and the carcinoma or cancer is chronic myelogenous leukemia (e.g., CML that is Philadelphia chromosome positive).

In some embodiments of the methods provided herein, the pharmaceutical ingredient is canertinib or a pharmaceutically acceptable salt thereof, and the carcinoma or cancer is esophageal squamous cell carcinoma.

In some embodiments of the methods provided herein, the pharmaceutical ingredient is dasatinib or a pharmaceutically acceptable salt thereof, and the carcinoma or cancer is acute lymphoblastic leukemia (e.g., ALL that is Philadelphia chromosome positive), or chronic myelogenous leukemia (e.g., CML that is Philadelphia chromosome positive).

In some embodiments of the methods provided herein, the pharmaceutical ingredient is dovitinib or a pharmaceutically acceptable salt thereof, and the carcinoma or cancer is bladder cancer.

In some embodiments of the methods provided herein, the pharmaceutical ingredient is erlotinib or a pharmaceutically acceptable salt thereof, and the carcinoma or cancer is non-small cell lung cancer (e.g., NSCLC that is metastatic and has certain EGFR gene mutations), or pancreatic cancer.

In some embodiments of the methods provided herein, the pharmaceutical ingredient is gefitinib or a pharmaceutically acceptable salt thereof, and the carcinoma or cancer is non-small cell lung cancer (e.g., NSCLC that has metastasized).

In some embodiments of the methods provided herein, the pharmaceutical ingredient is imatinib or a pharmaceutically acceptable salt thereof, and the carcinoma or cancer is acute lymphoblastic leukemia (e.g., adult (e.g., a subject at least 18 years old), child (e.g., a subject less than 18 years old), or a subject that is Philadelphia chromosome positive), chronic eosinophilic leukemia (i.e. hypereosinophilic syndrome), chronic myelogenous leukemia (e.g., in a subject that is Philadelphia chromosome positive), dermatofibrosarcoma protuberans, myelodysplastic neoplasm, myeloproliferative neoplasm, or systemic mastocytosis.

In some embodiments of the methods provided herein, the pharmaceutical ingredient is lapatinib or a pharmaceutically acceptable salt thereof, and the carcinoma or cancer is breast cancer (e.g., breast cancer that is advanced or has metastasized).

In some embodiments of the methods provided herein, the pharmaceutical ingredient is lestaurtinib or a pharmaceutically acceptable salt thereof, and the carcinoma or cancer is acute lymphoblastic leukemia (ALL) or acute myeloid leukemia (AML).

In some embodiments of the methods provided herein, the pharmaceutical ingredient is masitinib or a pharmaceutically acceptable salt thereof, and the carcinoma or cancer is acute lymphoblastic leukemia (e.g., adult (e.g., a subject at least 18 years old), child (e.g., a subject less than 18 years old), or a subject that is Philadelphia chromosome positive), chronic eosinophilic leukemia (i.e. hypereosinophilic syndrome), chronic myelogenous leukemia (e.g., in a subject that is Philadelphia chromosome positive), dermatofibrosarcoma protuberans, myelodysplastic neoplasm, myeloproliferative neoplasm, or systemic mastocytosis.

In some embodiments of the methods provided herein, the pharmaceutical ingredient is nilotinib or a pharmaceutically acceptable salt thereof, and the carcinoma or cancer is chronic myelogenous leukemia (e.g., CML that is Philadelphia chromosome positive).

In some embodiments of the methods provided herein, the pharmaceutical ingredient is pazopanib or a pharmaceutically acceptable salt thereof, and the carcinoma or cancer is renal cell carcinoma (e.g., renal cell carcinoma that is advanced), or soft tissue sarcoma (e.g., soft tissue sarcoma that is advanced).

In some embodiments of the methods provided herein, the pharmaceutical ingredient is sorafenib or a pharmaceutically acceptable salt thereof, and the carcinoma or cancer is hepatocellular carcinoma (e.g., HCC that cannot be removed by surgery), renal cell carcinoma (e.g., renal cell carcinoma that is advanced), or thyroid cancer (e.g., thyroid cancer in certain patients with progressive, recurrent, or metastatic disease).

In some embodiments of the methods provided herein, the pharmaceutical ingredient is vandetanib or a pharmaceutically acceptable salt thereof, and the carcinoma or cancer is thyroid cancer (e.g., metastatic) (e.g., medullary).

In some embodiments of the methods provided herein, the pharmaceutical ingredient is vatalanib or a pharmaceutically acceptable salt thereof, and the carcinoma or cancer is colorectal cancer (e.g., metastatic).

In some embodiments of the methods provided herein, the pharmaceutical ingredient is gemcitabine or a pharmaceutically acceptable salt thereof, and the carcinoma or cancer is bladder cancer, breast cancer (e.g., breast cancer in lymph nodes) (e.g., metastatic), non-small cell lung cancer (e.g., metastatic), ovarian cancer (e.g., metastatic), or pancreatic cancer.

In some embodiments of the methods provided herein, the pharmaceutical ingredient is sunitinib or a pharmaceutically acceptable salt thereof, and the carcinoma or cancer is gastric (stomach) cancer (e.g., metastatic), gastrointestinal cancer (e.g., gastrointestinal stromal tumor (e.g., imatinib-resistant)), or renal cell carcinoma.

In some embodiments of the compositions and methods provided herein, the pharmaceutical ingredient is terazosin or a pharmaceutically acceptable salt thereof.

In some embodiments of the compositions and methods provided herein, the pharmaceutical ingredient is one of the drugs of Table 1 and the carcinoma or cancer is an indication/use in Table 1 corresponding to the drug.

In some embodiments, the subject being treated is an adult (e.g., a subject at least 18 years old), a child (e.g., a subject less than 18 years old), or a subject (e.g., an adult or child) that is Philadelphia chromosome positive.

EXAMPLE 1

Preparation of Liquid Embolic Polymer

An emulsion provided herein is prepared and administered as described herein to a subject at an organ where dual blood supply is not available. The subject suffers from cancer of said organ. Said cancer is treated upon administration of the emulsion.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An emulsion, comprising a composition comprising:

a pharmaceutical ingredient;

a component of poppy seed oil selected from the group consisting of palmitic acid, stearic acid, oleic acid, linoleic acid, myristic acid, heptadecanoic acid, arachidic acid, γ-tocopherol, a glyceride and combinations thereof; and a biodegradable radiopaque polymeric particle comprising a visualization agent and: PLGA monomer; PLLA monomer; PLLA monomer and PLA monomer; PEG diacrylamide monomer, glycerol monomethacrylate monomer, 2-amino ethyl methacrylate monomer, and N,N-methylenebisacrylamide monomer; PEG diacrylamide monomer, amino propyl methacrylamide monomer, and 3-sulfopropyl acrylate potassium salt monomer; or PCL monomer and gelatin, wherein the pharmaceutical ingredient is axitinib, bosu-tinib, cabozantinib, canertinib, dasatinib, dovitinib, doxorubicin, epirubicin, erlotinib, gefitinib, gemcit-abine, idarubicin, imatinib, lapatinib, lestaurtinib, len-vatinib, masitinib, nilotinib, pazopanib, regorafenib, sorafenib, sunitinib, terazosin, vandetanib, vatalanib, oxaliplatin, or carboplatin, or a pharmaceutically acceptable salt thereof, wherein the visualization agent is an iodinated compound, barium sulfate, superparamagnetic iron oxide, or a gadolinium molecule, or a combination thereof, and wherein the visualization agent has a concentration of about 5% to about 65% by weight.

2. A Pickering emulsion comprising a composition com-prising:

a pharmaceutical ingredient;

a component of poppy seed oil selected from the group consisting of palmitic acid, stearic acid, oleic acid, linoleic acid, myristic acid, heptadecanoic acid, arachidic acid, γ-tocopherol, a glyceride and combina-tions thereof; and a biodegradable radiopaque polymeric particle compris-ing a visualization agent and: PLGA monomer; PLLA monomer; PLLA monomer and PLA monomer; PEG diacrylamide monomer, glycerol monomethacrylate monomer, 2-amino ethyl methacrylate monomer, and N,N-methylenebisacrylamide monomer; PEG diacryl-amide monomer, amino propyl methacrylamide mono-mer, and 3-sulfopropyl acrylate potassium salt mono-mer; or PCL monomer and gelatin, wherein the pharmaceutical ingredient is axitinib, bosu-tinib, cabozantinib, canertinib, dasatinib, dovitinib, doxorubicin, epirubicin, erlotinib, gefitinib, gemcit-abine, idarubicin, imatinib, lapatinib, lestaurtinib, len-vatinib, masitinib, nilotinib, pazopanib, regorafenib, sorafenib, sunitinib, terazosin, vandetanib, vatalanib, oxaliplatin, or carboplatin, or a pharmaceutically acceptable salt thereof, wherein the visualization agent is an iodinated compound, barium sulfate, superparamagnetic iron oxide, or a gadolinium molecule, or a combination thereof, and wherein the visualization agent has a concentration of about 5% to about 65% by weight.

3. A method of treating a vascular disorder comprising administering to a patient in need thereof the composition of claim 1.

4. A method of treating a vascular disorder comprising administering to a patient in need thereof the Pickering emulsion of claim 1.

5. The emulsion of claim 1, wherein the pharmaceutical ingredient is axitinib, bosutinib, cabozantinib malate, can-ertinib diHCl, dasatinib, dovitinib, doxorubicin HCl, epiru-bicin HCl, erlotinib HCl, gefitinib, gemcitabine, idarubicin HCl, imatinib methane-sulfonate, lapatinib toluene-sulfonate, lestaurtinib, lenvatinib mesylate, masitinib, nilo-tinib, pazopanib, regorafenib, sorafenib, sunitinib, terazosin, vandetanib, or vatalanib diHCl.

6. The emulsion of claim 1, wherein the pharmaceutical ingredient is oxaliplatin.

7. The emulsion of claim 1, wherein the biodegradable radiopaque polymeric particle is a biodegradable radiopaque polymeric nano-particle.

8. The emulsion of claim 1, wherein the biodegradable radiopaque polymeric particle comprises a visualization agent and a reaction product selected from the group con-sisting of: (1) a reaction product of 28% w/w of PEG 10,000 diacrylamide monomer, 68% w/w of glycerol monometh-acrylate monomer, 3% w/w of 2-amino ethyl methacrylate monomer, and 1% w/w of N,N-methylenebisacrylamide monomer; and (2) a reaction product of 40% w/w of PEG 10,000 diacrylamide monomer, 1% w/w of amino propyl methacrylamide monomer, and 59% w/w of 3-sulfopropyl acrylate potassium salt monomer.

9. The emulsion of claim 1, wherein the glyceride is selected from the group consisting of saturated dilinolein, oleo-dilinolein, trilinolein, and a combination thereof.

10. The emulsion of claim 1, wherein the composition comprises poppy seed oil.

11. The emulsion of claim 1, wherein the visualization agent is linked to PLGA monomer.

12. The emulsion of claim 1, wherein the visualization agent is an iodinated compound.

13. The emulsion of claim 1, wherein the visualization agent is triiodophenol.

14. The emulsion of claim 1, wherein the biodegradable radiopaque polymeric particle comprises barium sulfate and PLGA monomer.

15. The emulsion of claim 1, wherein the biodegradable radiopaque polymeric particle is hydrophobic.

16. The emulsion of claim 1, wherein the biodegradable radiopaque polymeric particle comprises a reaction product selected from the group consisting of: (1) a reaction product of a PLGA monomer and an initiator; (2) a reaction product of a PLLA monomer and an initiator; (3) a reaction product of a PLLA monomer and a PLA monomer and an initiator; (4) a reaction product of a PEG 10,000 diacrylamide mono-mer (28% w/w), glycerol monomethacrylate monomer (68% w/w), 2-amino ethyl methacrylate monomer (3% w/w), and N,N-methylenebisacrylamide monomer (1% w/w) initiated by ammonium persulfate and tetramethylene diamine; (5) a reaction product of a PEG 10,000 diacrylamide monomer (40% w/w), amino propyl methacrylamide monomer (1% w/w), and 3-sulfopropyl acrylate potassium salt monomer (59% w/w) initiated by ammonium persulfate and tetram-ethylene diamine; and (6) a reaction product of a PCL monomer and gelatin and an initiator.

* * * * *